(12) United States Patent
Prokop

(10) Patent No.: US 9,152,913 B2
(45) Date of Patent: Oct. 6, 2015

(54) UNIQUELY IDENTIFIABLE DRUG DOSAGE FORM UNITS

(71) Applicant: David Prokop, Sammamish, WA (US)

(72) Inventor: David Prokop, Sammamish, WA (US)

( * ) Notice: Subject to any disclaimer, the term of this patent is extended or adjusted under 35 U.S.C. 154(b) by 0 days.

(21) Appl. No.: 14/517,737

(22) Filed: Oct. 17, 2014

(65) Prior Publication Data

US 2015/0102099 A1   Apr. 16, 2015

Related U.S. Application Data

(63) Continuation of application No. 13/906,801, filed on May 31, 2013, now Pat. No. 8,888,005.

(60) Provisional application No. 61/811,616, filed on Apr. 12, 2013.

(51) Int. Cl.
| | |
|---|---|
| G06K 19/14 | (2006.01) |
| G06K 9/00 | (2006.01) |
| G06K 19/08 | (2006.01) |
| G06F 19/00 | (2011.01) |
| A61J 3/00 | (2006.01) |
| G06K 9/62 | (2006.01) |
| B41F 17/38 | (2006.01) |

(52) U.S. Cl.
CPC ............... *G06K 19/14* (2013.01); *A61J 3/007* (2013.01); *B41F 17/38* (2013.01); *G06F 19/3462* (2013.01); *G06K 9/00577* (2013.01); *G06K 9/6202* (2013.01); *G06K 19/086* (2013.01); *A61J 2205/00* (2013.01); *G06K 2009/0059* (2013.01)

(58) Field of Classification Search
CPC . G06K 19/14; G06K 9/00577; G06K 9/6302; G06K 2009/0059; G06K 19/086; G06F 19/3462; A61J 3/007; A61J 2105/00; B41F 17/38

See application file for complete search history.

(56) References Cited

U.S. PATENT DOCUMENTS

2003/0062422 A1*   4/2003   Fateley et al. ................. 235/494

* cited by examiner

*Primary Examiner* — Kristy A Haupt
(74) *Attorney, Agent, or Firm* — Perkins Coie LLP

(57) ABSTRACT

The present invention provides products, systems, and methods for the unique identification of individual drug dosage form units. The invention includes: random integrated optical identification marking of an individual drug unit; a lack of direct surface-to-surface contact between a marking instrument and the drug unit, i.e., deposition of a mark; drug unit image data based on the identification mark; a secondary product identifier associated with the individual drug unit; and comparing the marked drug unit to drug unit image data.

12 Claims, 6 Drawing Sheets

Pill Identifiers Variations round spheres
make 2D dots of different sizes
depth of identifier in pill Different Coloured Spheres Square Cubes
Rectangle bars
Threads Random Shapes Pill shape + Pill colour Random background patterns behind pill on blister pack Pill edge colouring
- random colours
- or sequences

UNIQUELY IDENTIFIABLE DRUG DOSAGE FORM UNITS

CROSS-REFERENCE TO RELATED APPLICATION(S)

This application is a continuation of U.S. patent application Ser. No. 13/906,801, filed May 31, 2013, which claims priority to U.S. Provisional Patent Application No. 61/811,616, filed Apr. 12, 2013, both of which are herein incorporated by reference in their entireties.

BACKGROUND

In the United States, commercially available individual solid oral drug dosage form units ("drug units") are not conventionally separable and uniquely identifiable on a per unit basis. Instead, each individual drug unit is identified based on its conformity to a uniform standard established for each drug product, such that drug units for a given drug product are typically indistinguishable from each other.

Current drug product identification is, in part, governed by Title 21 of the Code of Federal Regulations, Section 206.10, which provides a mechanism for the routine identification of solid oral dosage form drug products. That is, no drug product in a solid oral dosage form may be introduced or delivered for introduction into interstate commerce unless each of its drug units is clearly marked or imprinted with a "code imprint" that, in conjunction with the unit's size, shape, and color, permits the identification of the drug product and the manufacturer or distributor of the drug product. A code imprint can refer to any single letter or number or any combination of letters and numbers, including, e.g., words, company name, and National Drug Code, or a mark, symbol, logo, or monogram, or a combination of letters, numbers, and marks or symbols, assigned by a drug firm to a specific drug product. Such code imprints are usually uniformly coarsely embossed, debossed, engraved, stamped, or printed with ink onto or into each unit of a particular drug product as part of, or after, the manufacturing process.

While standardizing drug product appearance and requiring that each unit of a particular drug product conforms to the same criteria assists identification of drug units by comparison to a pre-set type for drug products generally, such uniformity also facilitates drug counterfeiting and obstructs the tracking and authentication of individual drug units. Once a counterfeiter is able to passably replicate the appearance of a single drug unit, production of mass quantities of drug units of a particular counterfeit drug product can proceed relatively unhindered. Counterfeiting is also aided, for example, by the ready commercial availability of tablet and pill manufacturing equipment, well-known and openly published fabrication methods, and fabrication methods and parameters that may be easily derived from direct observation of the code imprint and drug unit.

Efforts to create separable and uniquely identifiable drug units and drug unit authentication systems have been made. For example, the use of bar codes, engravings, stamps, etc., has been proposed as a way to uniquely identify individual drug units. However, such proposals require surface-to-surface contact between a marking instrument and each drug unit to identify each unit. Such direct surface-to-surface contact is undesirable for several reasons including, but not limited to, insertion of additional, expensive, slowing, and/or complicating steps into the process of manufacture, possible interference with other uniform drug product features useful for general product identification, and/or compromising the surface integrity and/or stability of the drug unit. Further, such efforts typically require that the end user have some sort of non-human machine visual or optical scanning device or reader to ascertain the meaning of, and to track and authenticate, each marked drug unit. The need for and reliance on such non-human analytical tools elevates the cost associated with using such marks and restricts patients and/or other end users' access and ability to independently authenticate marks.

SUMMARY

In its broadest sense, the present invention includes products, systems, and methods comprising: a random integrated optical identification mark on an individual product unit; product image data based on the identification mark; a secondary product identifier; and product unit authentication or tracking based on comparison of the identification mark to product image data.

In one embodiment, the present invention includes products, systems, and methods comprising: a random integrated optical identification mark on an individual product unit; product image data based on the identification mark; a secondary product identifier associated with the individual product unit; product unit authentication based on comparison of the identification mark to product image data; and providing electronic, computer, mobile, wireless, and/or web-based technology to facilitate comparison of an identification mark on an individual product unit with the product image data.

In another embodiment, the present invention includes products, systems, and methods comprising: a random integrated optical identification mark on an individual product unit, wherein the random integrated optical identification mark is made without direct surface-to-surface contact between a marking instrument and the product unit (herein the term "deposited" is used to describe an identification mark made without direct surface-to-surface contact between a marking instrument and the product unit); product image data based on the identification mark; a secondary product identifier associated with the individual product unit; product unit authentication based on comparison of the identification mark to product image data; and providing electronic, computer, mobile, wireless and/or web-based technology to facilitate comparison of a marked product unit with the product image data.

The present invention has wide applicability to the consumer products and the regulated products market because it provides for the first time elegant products, systems, and methods by which individual product units can be marked and authenticated. For example, the principles of the present invention and variations thereof may be applied to various products including, but not limited to, electronics hardware, fashion, publishing, medical devices and disposables (such as vials or syringes), medical records, educational and professional credentials, banknotes, contracts, professional service products, etc.

For our present purposes, however, this application specifically focuses on a preferred embodiment of the present invention for use with creating a secure drug product system involving the random marking of drug product units to facilitate authentication. Accordingly, the present invention can be used to protect public health and industry by providing an elegant solution to widespread drug counterfeiting, derivation, and authentication problems.

Conventional technologies related to drug product manufacture, optical and pattern recognition, and electronic, computer, mobile, wireless, and/or web-based technology may be used together with the present invention; nonetheless, it is also contemplated that further developments in each of these technology areas may be forthcoming that may also be used together with the present invention. Further, the present invention, as a whole, substantially builds on and significantly departs from each these widely divergent technological fields. Accordingly, the present invention gives rise to wholly new and fundamentally distinct products, systems, and methods and significant and unexpectedly superior results leading to easier, cheaper, faster, better, safer, more certain, and more user-friendly unit-level product authentication.

Contrary to conventional drug product identification regimes for individual solid oral drug units which involve the identification of drug units based on conformity to a general pre-set type, the present invention involves random integrated, i.e., non-separable, marking of drug units to track and authenticate individual drug units.

One of many advantages arising from the present invention is that it can be synergistically used with existing and/or forthcoming drug product identification systems and regimes. That is, the present invention may be synergistically used with other secure labeling practices (e.g., QR codes, bar codes, RFID systems, etc.) already used, or to be developed for use with, drug product packaging to track and authenticate individual drug units. A further advantage is that the present invention may be implemented on a per unit basis together with current "code imprint" requirements such that it need not interfere with other uniform drug product features. Such other secure labeling practices and/or drug product "code imprint" requirements may comprise one or more "secondary product identifiers" in accordance with the present invention.

Another principle advantage of the present invention is that marking is deposited, such that it does not require surface-to-surface contact between a marking instrument and each solid oral drug unit in order to uniquely mark each unit. This feature of the present invention fundamentally distinguishes the present invention over the use of bar codes, engravings, stamps, etc. Not only are marking products, systems, and methods that involve surface-to-surface contact more complicated, more time-consuming, and likely more expensive to implement, but such an approach also risks compromising the integrity and/or stability of the drug unit due to the increased pressure, temperature differentials, and extra handling involved with the direct marking contact required to uniquely identify each drug unit.

Another principle advantage of the present invention is that it is highly adaptable to accommodate a wide range of varying levels of tracking and authentication security. For example, the present invention may only require that a user visually compare a randomly marked drug unit with drug unit image data (e.g., one or more secured captured images) in order to authenticate the drug unit. Thus, the present invention delivers a means of drug authentication directly to the drug unit consumer that does not require that the consumer either have or know how to use fancy, expensive, and/or complicated image data tools. Accordingly, this invention empowers individual patients by giving them a greater measure of control over their own health care, since the present invention allows the patient to "trust their own eyes" using their own independent visual authentication. Alternatively, the present invention also permits an extremely high level of authentication security that can involve the use of secondary product identifiers, varying levels of image analysis, biometric data, etc.

DETAILED DESCRIPTION

Figure 1A:
FIGS. 1A, B, C, and D depict prior art marked drug units suitable for use with the present invention.
Figure 1B:
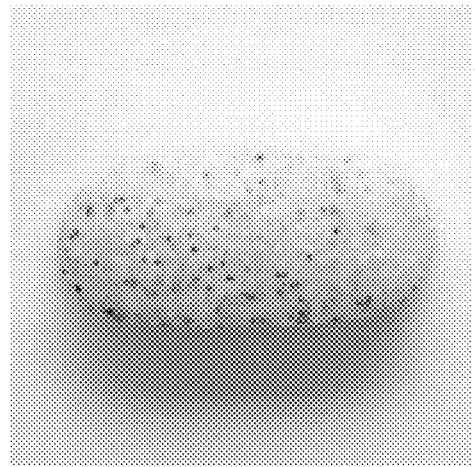
Figure 1C:
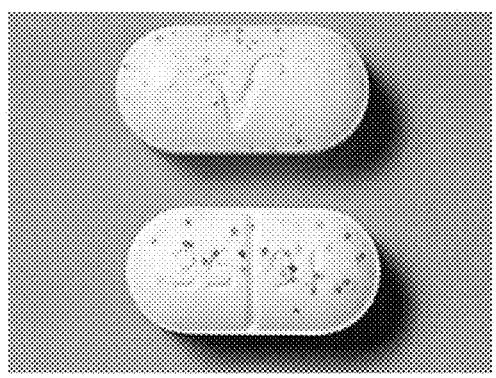
Figure 1D:
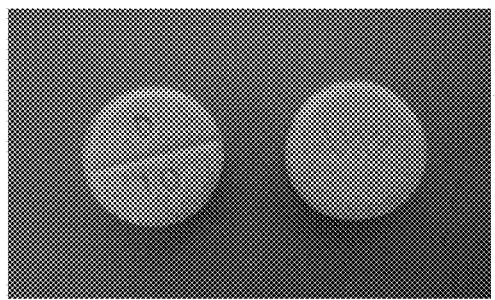
Figure 2A:
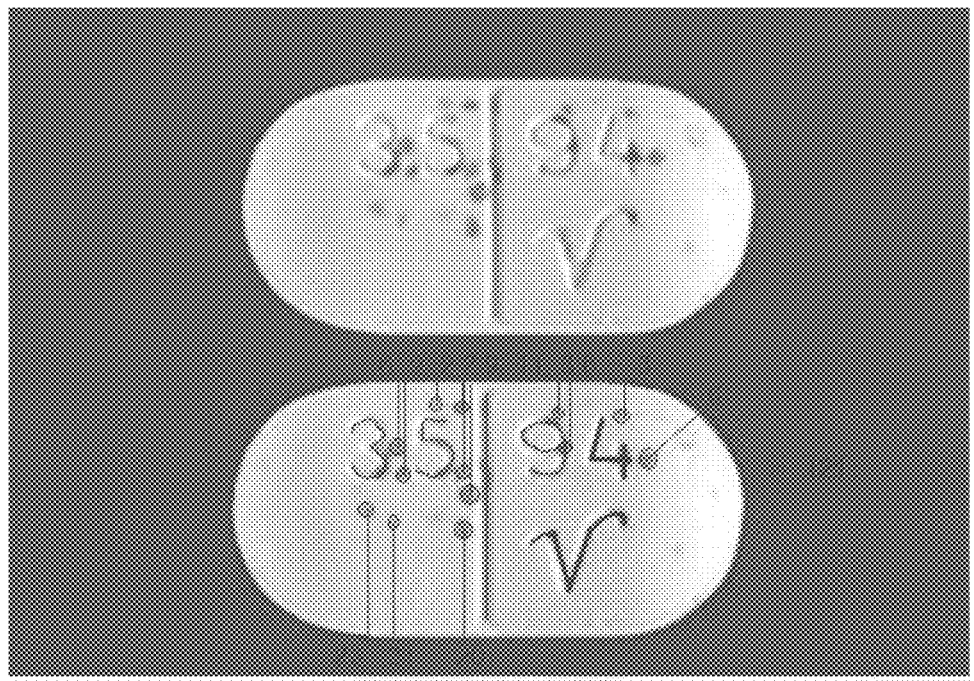
FIGS. 2A and B depict marked drug units including exemplary data indicators used in the analysis of marking information.
Figure 2B:
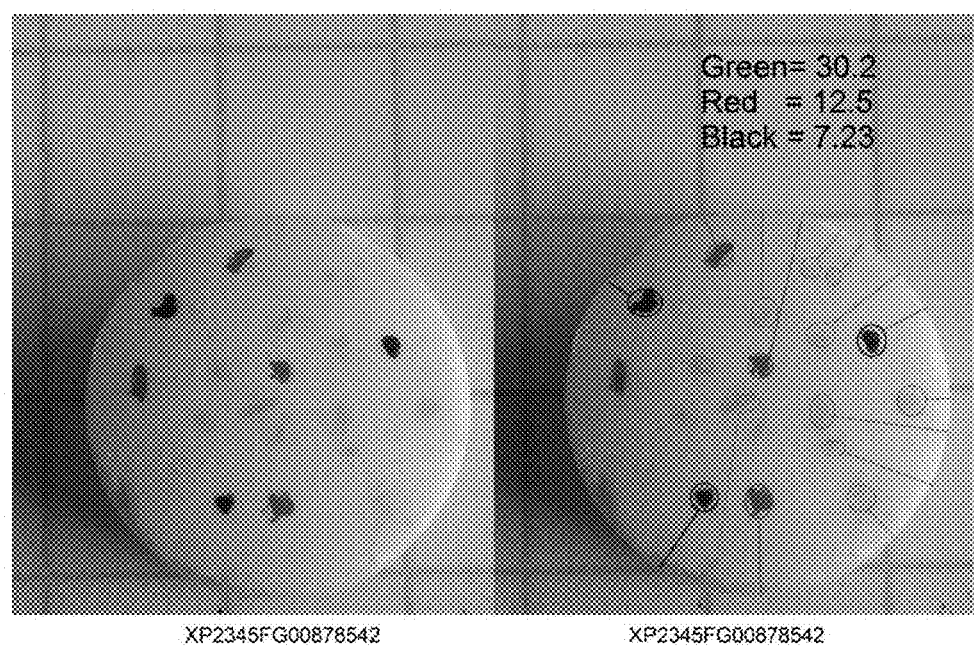
Figure 3:
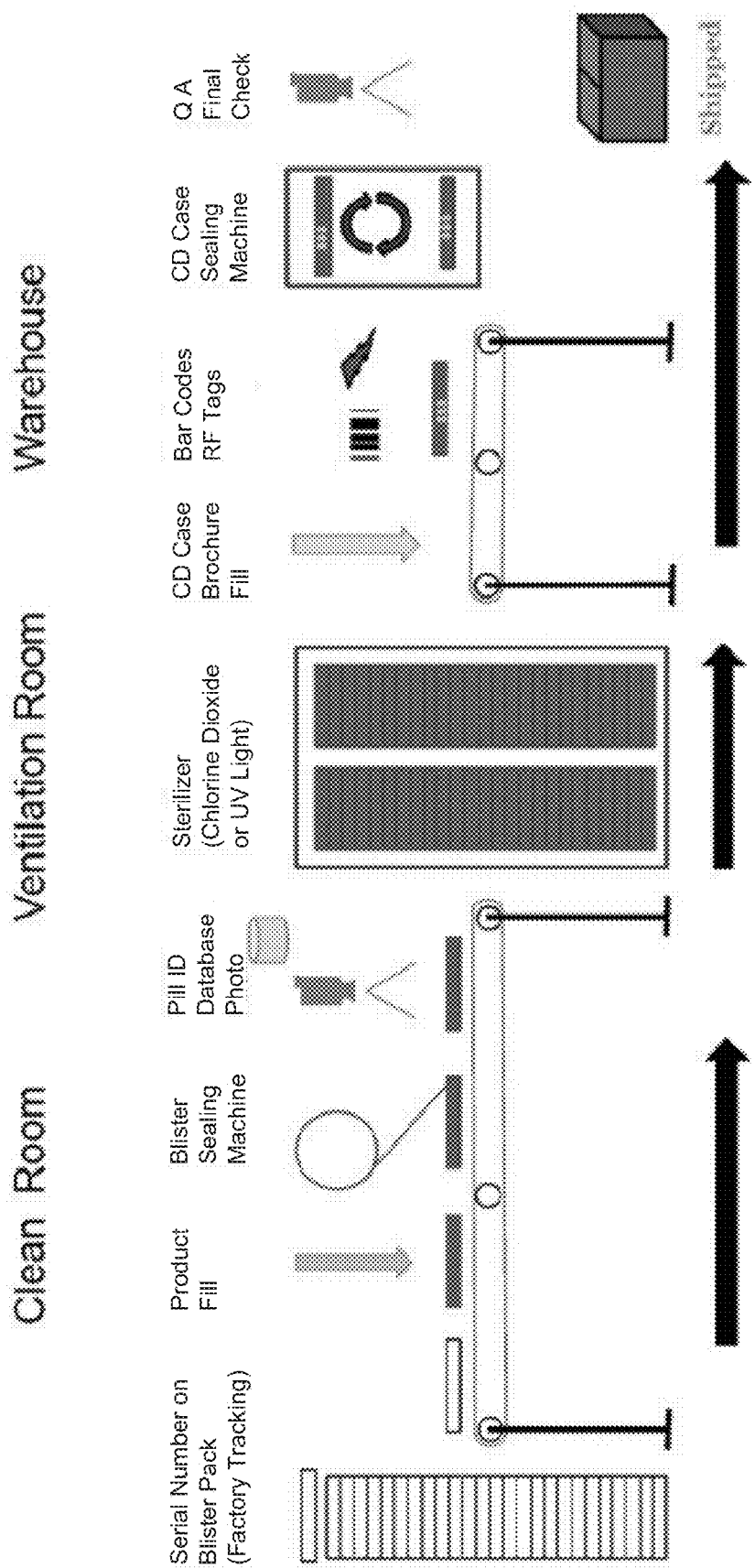
FIG. 3 depicts a packaging line station for drug units according to the present invention.
Figure 4:
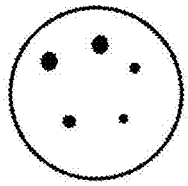
FIG. 4 depicts variations of drug unit markings that may be used in accordance with the present invention.
Figure 4:
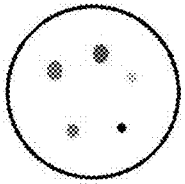
Figure 4:
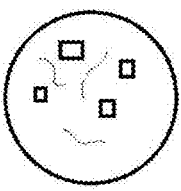
Figure 4:
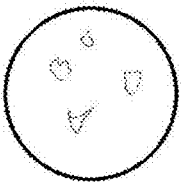
Figure 4:
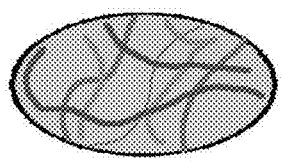
Figure 4:
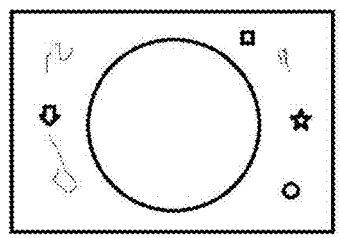
Figure 4:
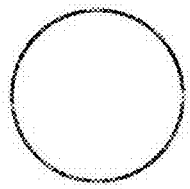
Figure 5:
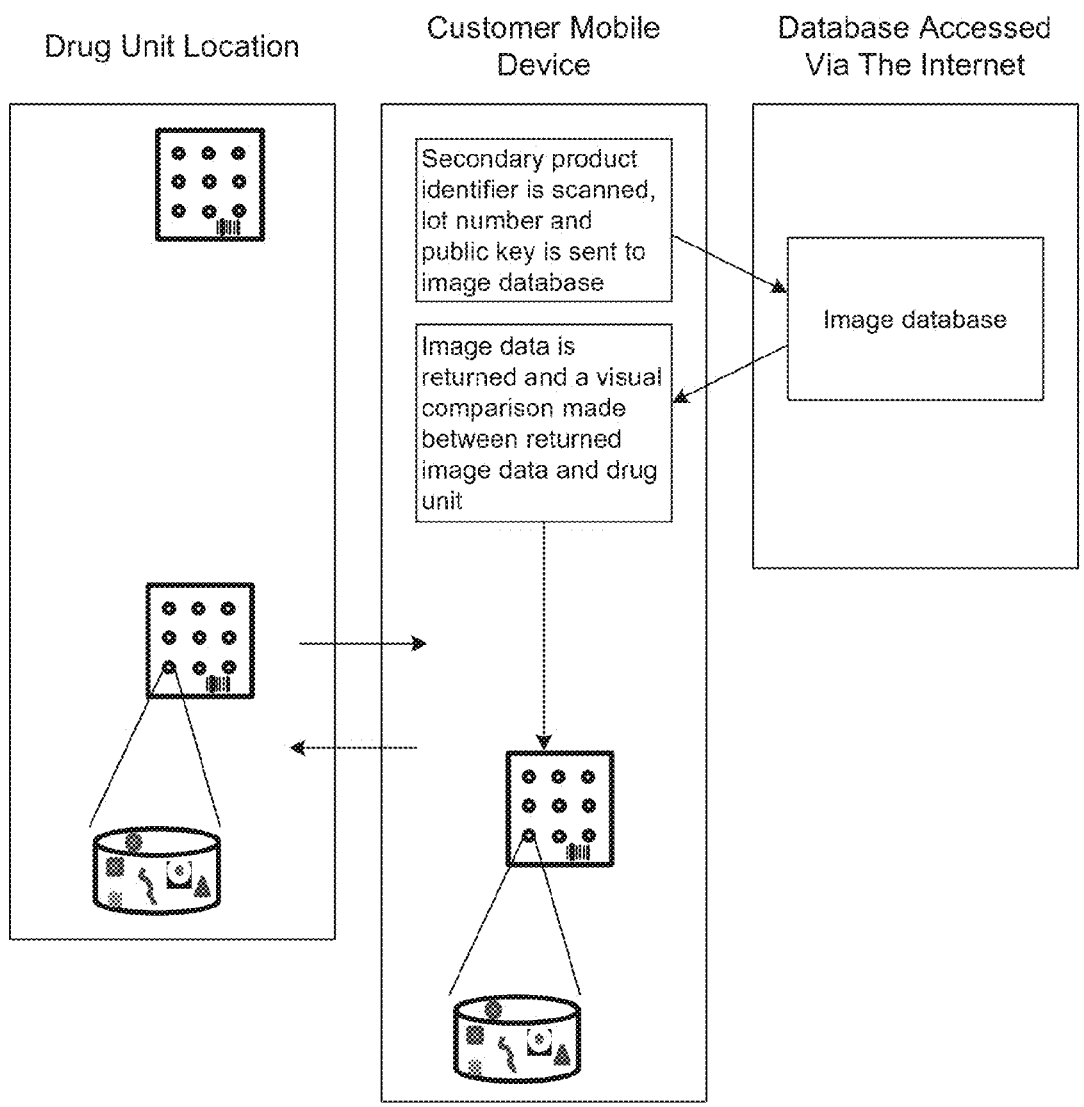
FIG. 5 provides a flow chart for an exemplary low security marked drug unit authentication process.
Figure 6:
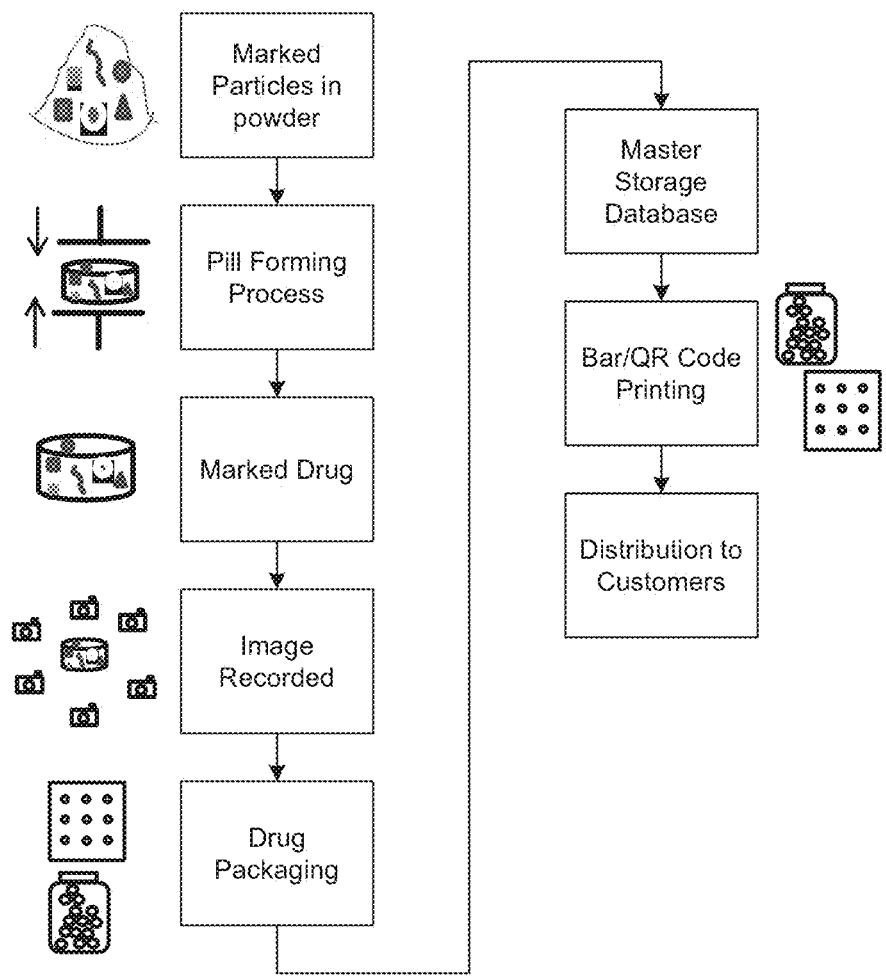
FIG. 6 provides a flow chart for an exemplary production process involving the integrated marking of drug units.

This invention comprises: random integrated optical identification marking of an individual drug unit; a lack of direct surface-to-surface contact between a marking instrument and the drug unit, i.e., deposition of a mark; drug unit image data based on the identification mark; a secondary product identifier associated with the individual drug unit; and comparing the marked drug unit to drug unit image data.

As used herein, the term "drug unit" refers to any solid and/or semisolid drug dosage unit for external or internal use in a human or animal subject, including, but not limited to, pills, tablets, capsules, lozenges, wafers, patches, therapeutic bandages, suppositories, and/or other solid or semisolid absorbables placed outside of or within a body. Drug units are in no way limited to solid oral drug dosage forms.

As used herein, the terms "mark," "marked," and "marking" refer to the random optical modification on the surface of and/or within each drug unit itself using one or more of dots, spots, shapes, splashes, sprays, splatters, speckles, threads, granules, or the like. Optionally, marking may comprise multiple tiers and, for example, additionally include one or more additional nano-blocks, nano-cubes, nano-particles, or nano-dice embedded in the drug unit.

As used herein, the term "secondary product identifier" refers to any additional drug product identification, such as QR codes, bar codes, RFID systems, etc., located on the drug product packaging (including boxes, bottles, lids, blister packs, labels, tags, information sheets, pamphlets, etc.), any associated information such as a receipt or a prescription, any uniform drug product characteristics, and/or any such removable component associated with the drug unit, etc.

As used herein, the term "internet website" refers to any electronically-aided communication, and may or may not involve the internet and may or may not operate in a public or private sphere.

1. Drug Unit Marking

Drug unit-level marking is based on random optical modification on the surface of and/or within each drug unit itself using one or more of dots, spots, shapes, splashes, splatters, speckles, threads, granules, or the like, to mark each drug unit. The random unit-level marking is done by deposition, i.e., without requiring any direct surface-to-surface contact between a marking device and the drug unit surface. Random marking of each drug unit itself can be accomplished by: (1) dotting, spotting, splashing, spraying, splattering, speckling, adding threads, and/or adding granule marking materials to the surface of the drug unit; and/or (2) mixing or otherwise integrating marking components (e.g., colored granules or other components) into a base formulation of the drug unit. The marking of each drug unit may involve one or more of various colors and/or materials. Optionally, marking may comprise multiple tiers involving both surface markings and one or more marking components integrated within the base formulation of the drug unit, such as threads, granules, nano-blocks, nano-cubes, nano-particles, nano-dice, etc.

Importantly, the marking of each drug unit is integral and inseparable from each drug unit itself. Accordingly, the marking cannot be removed from the drug unit without detectable destruction of the drug unit itself.

In a preferred embodiment, the marking materials can be used in a manner complementary to, and not impeding, drug product "code imprints" or other general characteristics used to identify particular drug products.

The visual or optical marking modification of the drug unit surface optionally allows for varying levels of penetration of one or more marking materials into the drug unit surface. Marked drug units may optionally include a protective, sealing, and/or otherwise image-enhancing top or outer coating.

The one or more marking materials can be applied to an entire external surface of a drug unit. Alternatively, the one or more marking materials can be applied to a particular surface or surfaces, location, segment, region, or limited area of the drug unit. The marking materials can be applied in a particular sequential order, series, and combination, or simultaneously. The marking materials may or may not generally conform to a general design or pattern, a set tolerance allowance for unit-to-unit variability, etc. The marking materials may be visible or invisible to the naked human eye, and/or visible or invisible with the aid of technology-enhanced vision, machine-aided, and/or computer-aided vision. The marking materials may alter the surface texture and/or tactile feel of the drug unit.

In one embodiment, materials and methods used for the random marking of drug units may, optionally, vary for each production lot, batch, production date, or any other such production groups. This production group level of variation can both 1) further aid drug unit-level tracking and authentication by further increasing the ability to provide unique and readily identifiable markings tied to other production information, and 2) decrease the likelihood of effective counterfeiting efforts by continued alteration of random marking production parameters.

Conventional methods and materials, including regulation approved (e.g., U.S. Food and Drug Administration ("FDA")) materials, can be used to accomplish the random marking of drug units. Accordingly, marking materials may comprise one or more inks, dyes, and/or color additives, including but not limited to, alumina (dried aluminum hydroxide), annatto extract, calcium carbonate, canthaxanthin, caramel, P-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, talc, titanium dioxide, aluminum powder, bronze powder, copper powder, zinc oxide, FD&C Blue No. 1, FD&C Blue No. 2, D&C Blue No. 4, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 3, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, FD&C Red No. 40, D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, and/or other FDA approved color additives.

2. Drug Unit Image Data

The present invention additionally involves capturing at least one image corresponding to each randomly marked drug unit. Multiple images of each drug unit may also be taken from one or more perspectives. Multiple images of each drug unit may also be taken under one or more different environmental, lighting, and speed conditions. Multiple images of each drug unit may also be taken at one or more discreet times.

Images of drug units may be taken separately for each individual drug unit. Images may also be taken of multiple drug units together. Images of drug units may be taken prior to, during, or after packaging. For example, one or more images may be taken of multiple drug units comprising parts of the same production run. Also, one or more images may be taken of multiple drug units packaged together in a transparent blister pack. In another example, one or more images of the contents of a particular pill bottle, including each of the individual drug units, may be taken.

Information, including secondary identifier information, can be associated with each captured image and/or drug unit image data. Additional information, such as the production details associated with the batch and lot number, production date, production location, source, type of drug, amount of drug, drug formulation, dosage information, expiration, prescription information, and storage information, etc., can also be associated with captured images and/or drug unit image data. Such additional information can be associated with the captured image at the time of image capture or at any time subsequent to image capture.

Image and/or any image-related data will be securely maintained. Secure maintenance of the image data and any image-related information can be performed by, for example, the drug manufacturer or company, a trusted third party or service, or any other secure intermediary.

In a preferred embodiment, image capture occurs upon the initial production of each randomly marked drug unit at the manufacturing plant, and as soon as possible after the random markings are "fixed," or static.

In another preferred embodiment, the images are captured under particular controlled environmental, lighting, flow rate, production, and/or throughput conditions. Image capture, according to the present invention, can be accomplished in production environments involving high-speed and high volumes of individual drug units. In an alternative embodiment, image data for marked drug units is captured for slowed, stalled, still, or non-moving drug units.

In addition to image capture, the present invention can include the use of conventional optical and/or pattern recognition technology based on captured images to authenticate, verify, and track marked drug units. Such optical and/or pattern recognition and image analysis can be performed for one or more images corresponding to each marked drug unit. The optical and/or pattern recognition and image analysis can be performed for each marked drug unit regardless of whether the drug unit has a flat, non-flat, regular, irregular, curved, three-dimensional, smooth, non-smooth, shaped, bumpy, etched, or otherwise non-uniform surface. In a preferred embodiment, the optical and/or pattern recognition technology can properly orient, compare, and/or combine or match images relating to the same drug unit but captured from different angles or perspectives relative to the drug unit and/or using only a portion of a marking.

The optical and/or pattern recognition and image analysis can involve any one or more of several characterization/analysis techniques. For a given marked drug unit, this includes, but is not limited to, measuring the distance of a random spot(s) center to edge of a drug unit, determining the equation of a line drawn from marking fragment to marking fragment; basing analysis on a grid x,y location, basing analysis on vector length and radius angle from the center point of the drug unit, etc. The optical and/or pattern recognition and image analysis can occur at any time contemporaneous with, or after, the one or more images of the drug unit are captured.

The optical and/or pattern recognition technology and the implementing electronics, computers, computer programs, computer applications, software, wireless, and/or mobile technologies and applications used with the present invention can also be especially adapted to interface with each randomly marked drug unit and captured image data and/or image-related data as discussed further below.

3. Secondary Product Identifiers

The present invention may also be synergistically used with additional separable marked product packaging, product labels, and/or other secondary product identifiers for drug product tracking and authentication (e.g., QR codes, bar codes, RFID systems, etc.). Such secondary product identifiers are conventionally used. The present invention, however, also contemplates the incorporation of additional secondary product identifiers yet to be developed.

4. Security

The present invention provides for varying and customizable levels of security and includes numerous low security, medium security, and high security embodiments. It is understood that myriad variations of the examples noted below are within the scope of the present invention.

According to the present invention, any drug unit image data is securely stored. For example, drug unit image data can be stored in a secured database. In a preferred embodiment, access to, and use of, the secure drug unit image data is triggered by user request. The present invention allows one or more of any of the drug unit manufacturer, the drug unit provider, the drug unit distributor, the drug unit retailer, the drug unit dispenser, and/or the drug unit consumer to set one or more of varying security levels.

In one preferred embodiment, the drug unit manufacturer sets a minimum security level that may be heightened by a downstream drug unit recipient seeking greater assurance as to drug unit authenticity.

An example of a low security embodiment that excludes the use of machine-aided vision or optics, but instead involves readily accessible human visual verification, provides that: (1) the user provides secondary product identifier information associated with the product packaging for a drug unit to an internet website; (2) the user receives a response that includes one or more drug unit images associated with the secondary product identifier information; and (3) the user makes a visual comparison of the drug unit with the one or more drug unit images to determine authenticity of the drug unit.

An example of a medium security embodiment involving visual and exchanged image data verification provides that: (1) the user provides secondary product identifier information associated with the product packaging for a drug unit and a photograph of the drug unit to an internet website; (2) the user receives a response regarding the authenticity of the drug unit that includes both a machine-vision analysis of the drug unit photograph provided by the user as compared to the captured image data for the drug unit and one or more drug unit images from a captured image database; and (3) the user, optionally, separately makes a visual comparison of the drug unit with the one or more drug unit images from the captured image data database to determine authenticity of the drug unit.

Another example of a medium security embodiment involving visual and exchanged image data verification provides that: (1) the user provides secondary product identifier information associated with the product packaging for a drug unit to an internet website; (2) the user takes a drug unit photograph that is analyzed by the user's image capture device; (3) the user's image capture device sends the analyzed image data to an internet website; (4) the analyzed image data prepared by the user's image capture device is compared to the captured image information for the drug unit in or from the captured image database; (5) the user receives a response regarding the authenticity of the product from the internet website and one or more drug unit images from the captured image database; and (6) the user, optionally, separately makes a visual comparison of the drug unit with the one or more drug unit images from the captured image database to determine authenticity of the drug unit.

Still another medium security embodiment additionally involves user-specific identification, which may include requiring that a user access code based on the product serial number be allocated to the specific person to have custody of the product before any drug unit image data is provided for comparison.

An example of a high security embodiment involves a secondary product identifier and exchanged image data verification as noted above in the medium security embodiments, and further involves requiring that a public encryption key be sent to an internet website along with a photograph of the user. In this high security embodiment, the public encryption key is matched to a private database key, and the photograph of the user is identity-matched to stored image information for the user. The user may be presented with the drug unit image data and the user image identity comparisons between the user-provided information and the private database may be shown side by side. Optionally, as presented, the compared image data may receive a numerical estimate of authentication match, such as "99.3% match" or a statement such as "accuracy of estimate is to within one of 48 billion."

Another example of a high security embodiment involves performing the drug unit authentication at a secure location. That is, the secure location includes any tools involved in the authentication including, for example, scanning (if necessary) the secondary product identifier and taking a photograph of the drug unit and, optionally, taking an identification photograph of the user. This securely obtained information is then compared to stored image information for the drug product, drug unit, and, optionally, the user. For example, the secured locations may be any of a pharmacy, hospital, clinic, distribution center, retailer, etc.

Whenever there is no match between compared images and/or image data, or a negative response is generated, a text message, website address or link, or telephone 1-800 hotline may be provided to the user to report the potential counterfeit product. The drug unit company and/or appropriate authorities may also be notified. Cash rewards or other incentives can be provided to the user to report and/or deliver the counterfeit material to an appropriate entity.

5. Systems

Computer programs, software, applications, electronic systems, and methods, including wireless and mobile applications, are part of the present invention.

In a preferred embodiment, the invention relates to a system involving: random integrated optical marking of individual drug product units and secondary product identifiers (e.g., QR codes, bar codes, RFID systems, etc.); captured, analyzed, stored, transmitted, and/or compared drug unit image data; and remote devices (such as smart phones, etc.) used for drug unit authentication.

Systems of the present invention can involve one or more computers, servers, computer programs, computer applications, wireless or mobile devices, electronic systems, software programs and/or applications, and/or the like, to authenticate, verify, and track marked drug units at multiple locations and/or over time by capturing, analyzing, storing, encrypting, communicating, and/or comparing drug unit image data.

In a preferred embodiment, drug unit image data is captured, analyzed, stored, and encrypted in a first location and the drug unit image data is communicated between and/or compared at at least a first location and a second location. In another embodiment, drug unit image data is captured, analyzed, stored, and optionally encrypted, in both a first location associated with drug unit creation and a second separate location associated with user authentication.

Communication and comparison of the drug unit image data can occur using public and/or private channels and can occur at one or more of any number of locations. In a preferred embodiment, communication and comparison of drug unit image data is done over the internet and involves at least one secured drug unit image data location. Locations according to the present invention can be numerous and are not geographically limited.

The present invention comprises a system for drug authentication comprising: a uniquely marked individual drug dosage form; one of optical and pattern recognition technology; and one of a computer, computer program, computer application, and/or software to collect, analyze, store, encrypt, transmit, or communicate information related to the uniquely marked individual drug dosage form. The unique mark of the individual drug dosage form is an integral part of the drug dosage form. The unique mark of the individual drug dosage form is one of on the surface of, impregnated within, and distributed throughout the drug dosage form. The optical or pattern recognition technology includes imaging information specific to the uniquely marked individual drug dosage form. The imaging information is collected from a three-dimensional surface of the uniquely marked individual drug dosage form.

A preferred embodiment the present invention, however, relates to a secure drug system comprising:

integral security marking directly on the surface of, impregnated on the surface of, or otherwise within the drug products themselves;

individual unique integral security marking for each solid and/or semisolid drug dosage unit, including, but not limited to, pills, tablets, capsules, lozenges, wafers, patches, therapeutic bandages, suppositories and/or other solid absorbables for external or internal use in a human or animal subject;

individual unique integral security marking for each production lot, batch, or other such production unit comprising solid or semisolid drug dosage forms;

individual unique integral security marking materials comprising one or more inks, dyes, and/or color additives, including but not limited to, alumina (dried aluminum hydroxide), annatto extract, calcium carbonate, canthaxanthin, caramel, P-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, talc, titanium dioxide, aluminum powder, bronze powder, copper powder, zinc oxide, FD&C Blue No. 1, FD&C Blue No. 2, D&C Blue No. 4, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 3, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, FD&C Red No. 40, D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, and/or other U.S. Food and Drug Administration approved color additives;

individual unique integral security marking materials comprising one or more inks, dyes, and/or color additives as applied in a particular sequential order, series, combination, and/or generally conforming to a general design or pattern, etc.;

individual unique integral security marking materials comprising one or more inks, dyes, and/or color additives, wherein the inks, dyes, and/or color additives are visible or invisible to the naked human eye, and/or visible or invisible with the aid of technology-enhanced vision or computer-aided vision;

optical and/or pattern recognition technology and computers, computer programs, computer applications, and/or software to interface with the individual unique integral security marking;

optical and/or pattern recognition technology and computers, computer programs, computer applications, and/or software to interface with the individual unique integral security marking, wherein each individual unique integral security marking may be in one or more various colors;

optical and/or pattern recognition technology and computers, computer programs, computer applications, and/or software to interface with the individual unique integral security marking, and to analyze, capture, store, and/or compare an image and/or information associated with the individual unique integral security marking;

optical and/or pattern recognition technology and computers, computer programs, computer applications, and/or software to interface with the individual unique integral security marking, to analyze, capture, store, encrypt, and/or compare an image and/or information associated with the individual unique integral security marking, and to transmit, relay, encrypt, and/or communicate the image and/or information with one or more other computers, including mobile devices such as smart phones, etc.;

optical and/or pattern recognition technology and computers, computer programs, computer applications, and/or software to interface with the individual unique integral security marking, to analyze, capture, store, encrypt, and/or compare an image and/or information associated with the individual unique integral security marking, to transmit, relay, encrypt, and/or communicate the image and/or information to and/or from a first location of image and/or information analysis, capture, storage, and/or comparison to and/or from a second location involving one or more computers and/or devices that are local and/or distant;

optical and/or pattern recognition technology and computers, computer programs, computer applications, and/or software to interface with the individual unique integral security marking, to analyze, capture, store, encrypt, and/or compare an image and/or information associated with the individual unique integral security marking, to transmit, relay, encrypt, and/or communicate the image and/or information to and/or from a first location of image and/or information analysis, capture, storage, encryption, and/or comparison to and/or from a second location involving one or more computers and/or devices that are local and/or distant, wherein the transmission, relay, and/or communication is via a private network and/or via the internet and may, or may not, involve one or more computers, servers, and/or mobile devices;

optical and/or pattern recognition technology and computers, computer programs, computer applications, and/or software to interface with the individual unique integral security marking, to analyze, capture, store, encrypt, and/or compare an image and/or information associated with the individual unique integral security marking, to transmit, relay, encrypt, and/or communicate the image and/or information to and/or from a first location of image and/or information analysis, capture, storage, encryption, and/or comparison to and/or from a second location involving one or more computers and/or devices that are local and/or distant, wherein the transmission, relay, and/or communication is via a private network and/or via the internet and may, or may not, involve one or more computers, servers, and/or mobile devices, and wherein the second location also includes an optical and/or pattern recognition technology and computers, computer programs, computer applications, and/or software to interface with the individual unique integral security marking to authenticate, encrypt, verify, and track the marked product;

optical and/or pattern recognition technology and computers, computer programs, computer applications, and/or software such as that described above available in a web-based application for use on mobile devices, including smart phones, etc.;

optical and/or pattern recognition technology and computers, computer programs, computer applications, and/or software to interface with the individual unique integral security marking, wherein each individual unique integral security marking may be on a non-flat, three-dimensional, smooth, or non-smooth surface;

a controlled environment optical and/or pattern recognition technology and software, wherein the controlled environment may involve particular lighting, high-speed, high volumes, and/or high throughput;

any method of practicing the invention involving any of the various embodiments described above;

any method of practicing the invention involving any of the various embodiments described above to counter, prevent, or reduce the counterfeit drug trade;

any method of practicing the invention involving any of the various embodiments described above to assure an end user subject that the drug they have is authentic and its origin and history is known; and any method of practicing the invention involving any of the various embodiments described above wherein a user of a computer and/or mobile device, including an individual patient, doctor, or pharmacist, can authenticate, verify, and track a product marked and analyzed in accordance with this invention.

6. Methods

Recipients of drug units marked with random optical integrated identification markings, such as patients, pharmacists, hospitals, clinics, physicians, nurses, etc., can use secondary product identifiers associated with the drug units, hardware incorporating or implementing appropriate computer software, computer applications, computer programs, wireless technologies, mobile applications, and an "internet website" to use drug unit image data, for comparing and authenticating the drug units.

In one preferred embodiment, recipients use visual image data corresponding to secondary product identifiers to visually verify and confirm drug unit authenticity without machine-aided or computer-aided vision. For example, a user may obtain one or more captured image photographs corresponding to the drug unit and, simply by looking, authenticate the drug unit.

In another embodiment, downstream drug unit recipients can use machine-aided or computer-aided assistance together with secondary product identifiers associated with the drug product to optically compare, verify, and confirm drug unit authenticity based on drug unit image data. For example, a downstream recipient may take and send one or more photographs corresponding to the drug unit for comparison to potentially corresponding drug unit image data to authenticate the drug unit.

The present invention includes any method of practicing the invention according to any disclosure provided in this application including any of the various embodiments described above. The present invention also includes any method of practicing the invention to counter, prevent, or reduce the counterfeit drug trade. The present invention also includes any method of practicing the invention to ensure drug unit authenticity and provide confidence to a user that the drug they have is authentic and its origin and history is known.

I claim:

1. A drug unit authentication system, comprising a plurality of drug units, each drug unit containing a drug common to the plurality of drug units, and each drug unit having a deposited random integrated optically identifiable marking on a surface of or within a drug unit, wherein the marking of each drug unit in the plurality of drug units has a size, shape, location or distribution unique and differentiatable from the markings of all other of the drug units in the plurality of drug units, wherein each drug unit in the plurality of drug units has a secondary product identifier common to the plurality of the drug units and related to the common drug of the plurality of drug units, wherein the marking is configured for use in a comparison of a selected one of the drug units and drug unit marking data associated with the selected one of the drug units and being related to the markings and the second product identifier for the selected one of the drug units.

2. The system of claim 1 wherein the deposited random integrated optically identifiable marking includes one or more of dots, spots, shapes, splashes, sprays, splatters, speckles, threads, and granules.

3. The system of claim 1 wherein the deposited random integrated optically identifiable marking is both on a surface of and within the drug unit.

4. The system of claim 1, further comprising a comparator configured to perform an optical comparison of the selected one of the drug units and the drug unit marking data.

5. The system of claim 1, further comprising a comparator configured to perform pattern recognition comparison of the selected one of the drug units and the drug unit marking data.

6. The system of claim 5 wherein the comparator performs pattern recognition based upon one or more equations of lines between portions of the integrated optically identifiable marking, as a function of vector length and radius angle relative to a selected frame of reference.

7. The system of claim 1 wherein the drug unit marking data comprises image information based on the deposited random integrated optically identifiable marking.

8. The system of claim 1 wherein the drug unit marking data further comprises information associated with the secondary product identifier.

9. The system of claim 1 wherein the secondary product identifier is a quick response code, bar code, or a radio-frequency identification system.

10. The system of claim 1, further comprising human-readable drug unit marking data.

11. The system of claim 1, further comprising human-readable drug unit image data.

12. The system of claim 1 wherein the drug unit marking data comprises image data unique to a single one of the plurality of drug units based upon an image of the marking of single one of the plurality of drug units.

* * * * *